US012623021B2

(12) United States Patent
Söderlund

(10) Patent No.: US 12,623,021 B2
(45) Date of Patent: May 12, 2026

(54) MEDICAMENT DELIVERY DEVICE COMPONENT

(71) Applicant: SHL MEDICAL AG, Zug (CH)

(72) Inventor: Marcus Söderlund, Lidingö (SE)

(73) Assignee: SHL Medical AG, Zug (CH)

( * ) Notice: Subject to any disclaimer, the term of this patent is extended or adjusted under 35 U.S.C. 154(b) by 777 days.

(21) Appl. No.: 17/798,646

(22) PCT Filed: Nov. 20, 2020

(86) PCT No.: PCT/EP2020/082945
§ 371 (c)(1),
(2) Date: Aug. 10, 2022

(87) PCT Pub. No.: WO2021/185471
PCT Pub. Date: Sep. 23, 2021

(65) Prior Publication Data
US 2023/0057609 A1    Feb. 23, 2023

(30) Foreign Application Priority Data

Mar. 20, 2020    (EP) ..................................... 20164587

(51) Int. Cl.
A61M 5/20        (2006.01)
A61M 5/31        (2006.01)

(52) U.S. Cl.
CPC ................ A61M 5/20 (2013.01); A61M 5/31 (2013.01)

(58) Field of Classification Search
CPC ............ A61J 1/16; A61M 2005/31508; A61M 5/31566; A61M 5/315; A61M 5/24
See application file for complete search history.

(56) References Cited

U.S. PATENT DOCUMENTS 5,997,511 A * 12/1999 Curie .................... A61M 5/322
604/110
6,221,046 B1 * 4/2001 Burroughs ........ A61M 5/31551
604/207

(Continued)

FOREIGN PATENT DOCUMENTS

EP        2305335 A1    4/2011
EP        3302642 B1    9/2019

(Continued)

OTHER PUBLICATIONS

International Search Report and Written Opinion for Int. App. No. PCT/EP2020/082945, mailed Dec. 10, 2020.

*Primary Examiner* — Scott J Medway
(74) *Attorney, Agent, or Firm* — McDonnell Boehnen Hulbert & Berghoff LLP

(57) ABSTRACT

Medicament delivery device components that compensate for manufacturing tolerances are presented, where the medicament delivery device component can have a base portion extending in an axial direction relative to an axis, a compensation member having a first portion attached to the base portion and a second portion attached to the first portion and spaced apart from the base portion in the axial direction. The second portion can have a disc extending around the axis in the circumferential direction and a protrusion extending from the disc in the axial direction, wherein the protrusion is spaced apart from the first portion in the circumferential direction. At least part of the disc is configured to flex relative to the base portion when acted on by a force in the axial direction.

18 Claims, 9 Drawing Sheets

(56) References Cited

U.S. PATENT DOCUMENTS

| | | | | |
|---|---|---|---|---|
| 6,899,698 | B2 * | 5/2005 | Sams | A61M 5/31551 |
| | | | | 604/211 |
| 7,325,544 | B2 | 2/2008 | Bruna | |
| 8,048,035 | B2 * | 11/2011 | Mesa | A61M 5/3202 |
| | | | | 604/198 |
| 8,257,318 | B2 * | 9/2012 | Thogersen | A61M 5/31585 |
| | | | | 604/110 |
| 8,647,299 | B2 | 2/2014 | Stamp | |
| 8,708,972 | B2 * | 4/2014 | Christiansen | A61M 5/00 |
| | | | | 604/218 |
| 9,149,580 | B2 | 10/2015 | Jugl et al. | |
| 9,757,520 | B2 | 9/2017 | Corrigan | |
| 10,786,628 | B2 * | 9/2020 | Jacobsen | A61M 5/31515 |
| 10,898,646 | B2 * | 1/2021 | Klintenstedt | A61M 5/315 |
| 11,623,047 | B2 * | 4/2023 | Alkhatib | A61M 5/3202 |
| | | | | 604/506 |
| 12,434,008 | B1 * | 10/2025 | Hee-Hanson | A61M 5/31565 |
| 2007/0021718 | A1 * | 1/2007 | Burren | G01F 11/027 |
| | | | | 604/110 |
| 2017/0348489 | A1 | 12/2017 | Hirschel et al. | |
| 2018/0161504 | A1 | 6/2018 | Kemp et al. | |
| 2018/0169338 | A1 | 6/2018 | Mosebach et al. | |

FOREIGN PATENT DOCUMENTS

| | | | |
|---|---|---|---|
| WO | 2010/139635 | A1 | 12/2010 |
| WO | 2012/064259 | A1 | 5/2012 |
| WO | 2014/020000 | A1 | 2/2014 |
| WO | 2016/169756 | A1 | 10/2016 |
| WO | 2016/193341 | A1 | 12/2016 |
| WO | 2016/193355 | A1 | 12/2016 |
| WO | 2016/193374 | A1 | 12/2016 |
| WO | 2017/157396 | A1 | 9/2017 |
| WO | 2017/186435 | A1 | 11/2017 |

* cited by examiner

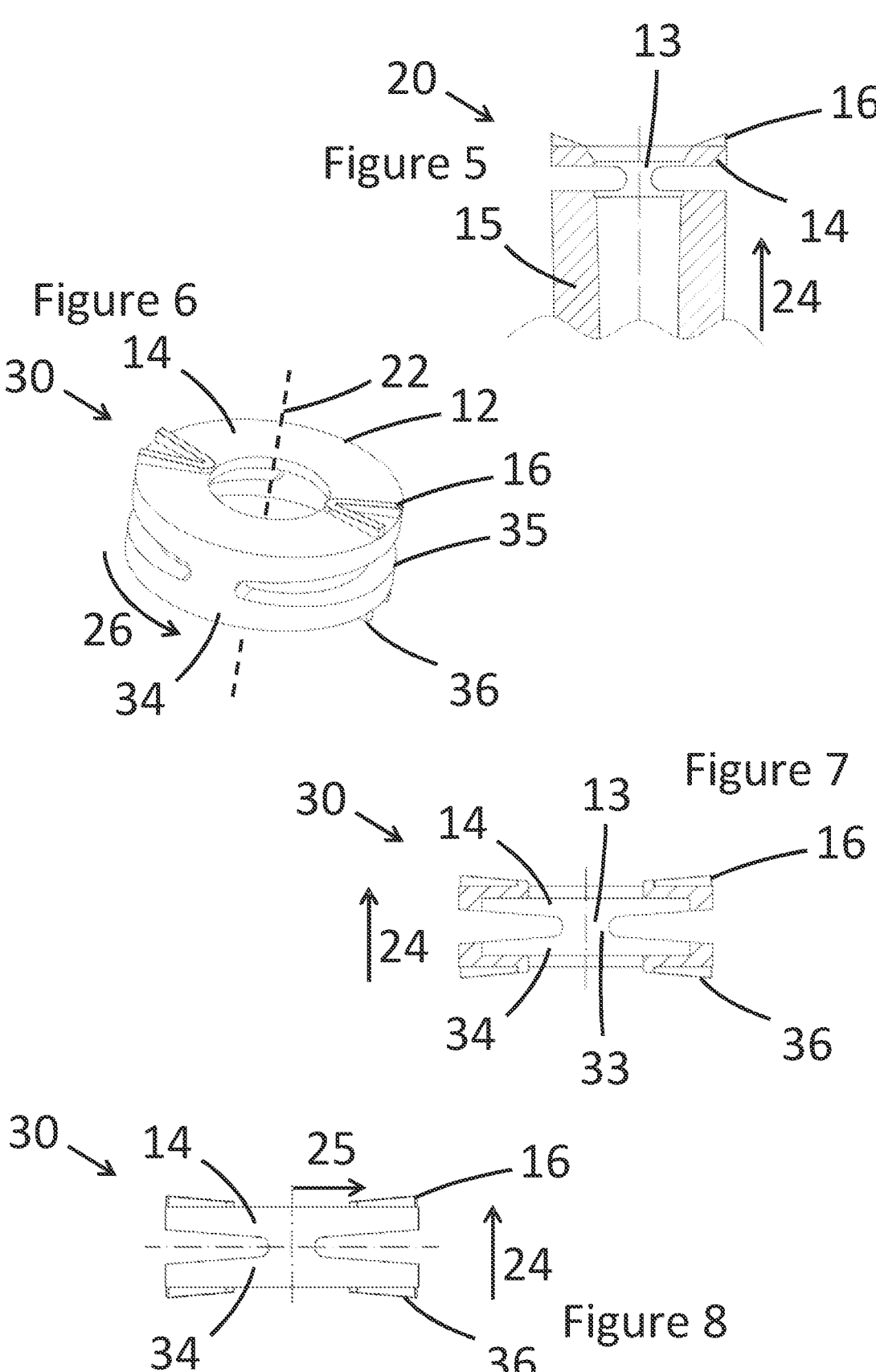

10

24

66
16
12
15

50

12
22
14
14
13
15
26
13

70  Figure 21          Figure 22
70
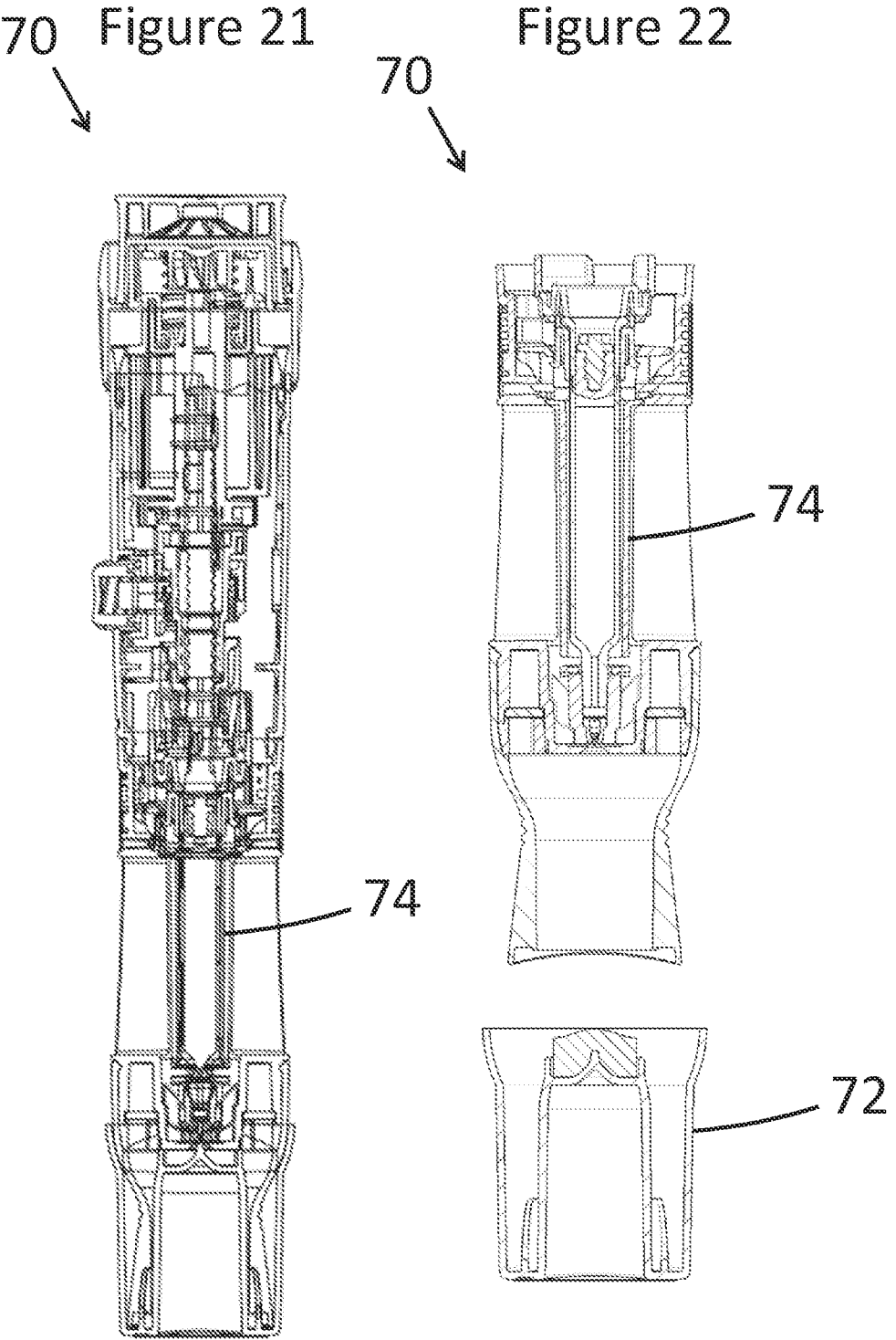
74
74
72

MEDICAMENT DELIVERY DEVICE COMPONENT

CROSS REFERENCE TO RELATED APPLICATIONS

The present application is a U.S. National Phase Application pursuant to 35 U.S.C. § 371 of International Application No. PCT/EP2020/082945 filed Nov. 20, 2020, which claims priority to European Patent Application No. 20164587.6 filed Mar. 20, 2020. The entire disclosure contents of these applications are herewith incorporated by reference into the present application.

TECHNICAL FIELD

The present disclosure concerns a medicament delivery device component, and particularly a medicament delivery device component for compensating manufacturing tolerance comprising a compensating member.

BACKGROUND

Medicament delivery devices are often made of a large number of different parts which are then fitted together. Although the accuracy of manufacture of these parts is typically high, there is still some need for tolerance within the assembled medicament delivery devices to allow for slight differences in the size of individual components due to manufacturing variability. With this in mind, the applicant has appreciated that improved tolerance management within medicament delivery devices would be desirable.

SUMMARY

The present disclosure is defined by the appended claims, to which reference should now be made.

In the present disclosure, when the term "distal direction" is used, this refers to the direction pointing away from the dose delivery site during use of the medicament delivery device. When the term "distal part/end" is used, this refers to the part/end of the delivery device, or the parts/ends of the members thereof, which under use of the medicament delivery device is/are located furthest away from the dose delivery site. Correspondingly, when the term "proximal direction" is used, this refers to the direction pointing towards the dose delivery site during use of the medicament delivery device. When the term "proximal part/end" is used, this refers to the part/end of the delivery device, or the parts/ends of the members thereof, which under use of the medicament delivery device is/are located closest to the dose delivery site.

Further, the terms "longitudinal", "longitudinally", "axially" and "axial" refer to a direction extending from the proximal end to the distal end and along the device or components thereof, typically in the direction of the longest extension of the device and/or component.

Similarly, the terms "transverse", "transversal" and "transversally" refer to a direction generally perpendicular to the longitudinal direction.

Generally, all terms used in the claims are to be interpreted according to their ordinary meaning in the technical field, unless explicitly defined otherwise herein. All references to a/an/the element, apparatus, member, component, means, etc. are to be interpreted openly as referring to at least one instance of the element, apparatus, member component, means, etc., unless explicitly stated otherwise.

A first aspect of the disclosure concerns a medicament delivery device component for compensating manufacturing tolerance, the medicament delivery device component comprising a base portion extending in an axial direction relative to an axis, a compensation member comprising a first portion attached to the base portion and a second portion attached to the first portion and spaced apart from the base portion in the axial direction, wherein the second portion comprises a disc extending around the axis in the circumferential direction and a protrusion extending from the disc in the axial direction, wherein the protrusion is spaced apart from the first portion in the circumferential direction, wherein at least part of the disc is configured to flex relative to the base portion when acted on by a force in the axial direction.

Medicament delivery device components of this type can compensate for manufacturing tolerances. In particular, they can compensate for manufacturing tolerances in the axial direction, such as limited accuracy of component length within a medicament delivery device. The distances that would be compensated for would typically be small, for example 1 to 5 mm, although larger or smaller distances could also be compensated for in some embodiments. This present disclosure can therefore allow for cheaper manufacture, since lower accuracy production can be tolerated. In addition, the present disclosure can stop parts of a device from rattling.

In some embodiments, the disc extends around the axis in a plane perpendicular to the axis when the disc is in an unbiased state. In some embodiments, the base portion is tubular. In some embodiments, the protrusion extends from a face of the disc, wherein the face of the disc faces away from the base portion.

In some embodiments, the portion of the protrusion furthest from the axis extends further away from the base portion than the portion of the protrusion closest to the axis. A protrusion of this shape can reduce stress on components. This can therefore increase component and device lifetime, and can allow for lighter or cheaper components.

In some embodiments, the base portion is a second compensation member, the second compensation member comprising a first portion of the second compensation member, wherein the first portion of the second compensation member is attached to the first portion of the compensation member and a second portion of the second compensation member, wherein the second portion of the second compensation member is attached to the first portion of the second compensation member and is spaced apart from the compensation member in the axial direction. This can provide a greater compensation range than a single compensation member, and can provide compensation in a standalone component.

In some embodiments, the second portion of the second compensation member comprises a disc extending around the axis in the circumferential direction and a protrusion extending from the disc in the axial direction, and wherein the protrusion is spaced apart from the first portion of the second compensation member in the circumferential direction.

A second aspect of the disclosure concerns a medicament delivery device component for compensating manufacturing tolerance, the medicament delivery device component comprising a compensation member and a second compensation member attached to the compensation member, the medicament delivery device component extending in an axial direction relative to an axis, the compensation member comprising a first portion and a second portion, the second compensation member comprising a first portion and a second portion, wherein the first portion of the compensation member and the first portion of the second compensation member are attached to each other, wherein the second portion of the compensation member is attached to the first portion of the compensation member and is spaced apart from the second compensation member in the axial direction, and wherein the second portion of the compensation member is configured to flex relative to the second compensation member when acted on by a force in the axial direction, wherein the second portion of the second compensation member is attached to the first portion of the second compensation member and is spaced apart from the compensation member in the axial direction when the medicament delivery device component is in an unbiased state, and wherein the second portion of the second compensation member is configured to flex relative to the compensation member when acted on by a force in the axial direction.

In some embodiments, the medicament delivery device component comprises a protrusion extending from the second portion of the compensation member, wherein the protrusion extends in the axial direction, and wherein the protrusion is spaced apart from the first portion of the second compensation member in the circumferential direction.

In some embodiments, the medicament delivery device component comprises a protrusion extending from the second portion of the second compensation member, wherein the protrusion extends in the axial direction, and wherein the protrusion is spaced apart from the first portion of the compensation member in the circumferential direction.

In some embodiments, the medicament delivery device component consists of the first compensation member and the second compensation member. In some embodiments, the compensation member is the same as the second compensation member. In some embodiments, the medicament delivery device component is a single integrally formed part.

A third aspect of the disclosure concerns a medicament delivery device comprising a medicament delivery device component described above. In some embodiments, the medicament delivery device is an inhaler, an auto-injector or a pen injector.

A fourth aspect of the disclosure concerns a medicament delivery device component for compensating manufacturing tolerance, the medicament delivery device component comprises a base portion and a compensation member, wherein the base portion extends in an axial direction relative to an axis, wherein the compensation member comprises a first portion attached to the base portion and a second portion attached to the first portion and spaced apart from the tubular body in the axial direction, wherein at least part of the second portion is configured to move relative to the base portion when acted on by a force in the axial direction, wherein the base portion comprises a disc extending around the axis in the circumferential direction and a protrusion extending from the disc in the axial direction, wherein the protrusion is spaced apart from the first portion in the circumferential direction (e.g. FIG. 7), or the base portion comprises a ring (e.g. FIG. 14), or the base portion comprises a tubular portion (e.g. FIG. 1). In some embodiments, the medicament delivery device component consists of a base portion and a compensation member. In some embodiments, the base portion consists of a disc and a protrusion, of a ring, or of a tubular portion.

BRIEF DESCRIPTION OF THE DRAWINGS

Embodiments of the present disclosure will now be described by way of example only and with reference to the accompanying drawings, in which:

FIG. 5 shows a cross-sectional side view of the second example of a medicament delivery device component.

FIG. 6 shows a perspective view of a third example of a medicament delivery device component.

FIG. 7 shows a cross-sectional side view of the third example of a medicament delivery device component.

FIG. 8 shows a side view of the third example of a medicament delivery device component.

FIG. 21 shows a cross-sectional side view of an inhaler with a medicament delivery device component as described herein.

FIG. 22 shows a cross-sectional side view of part of the inhaler of FIG. 21.

DETAILED DESCRIPTION

Figures 1, 2, 3, 4:
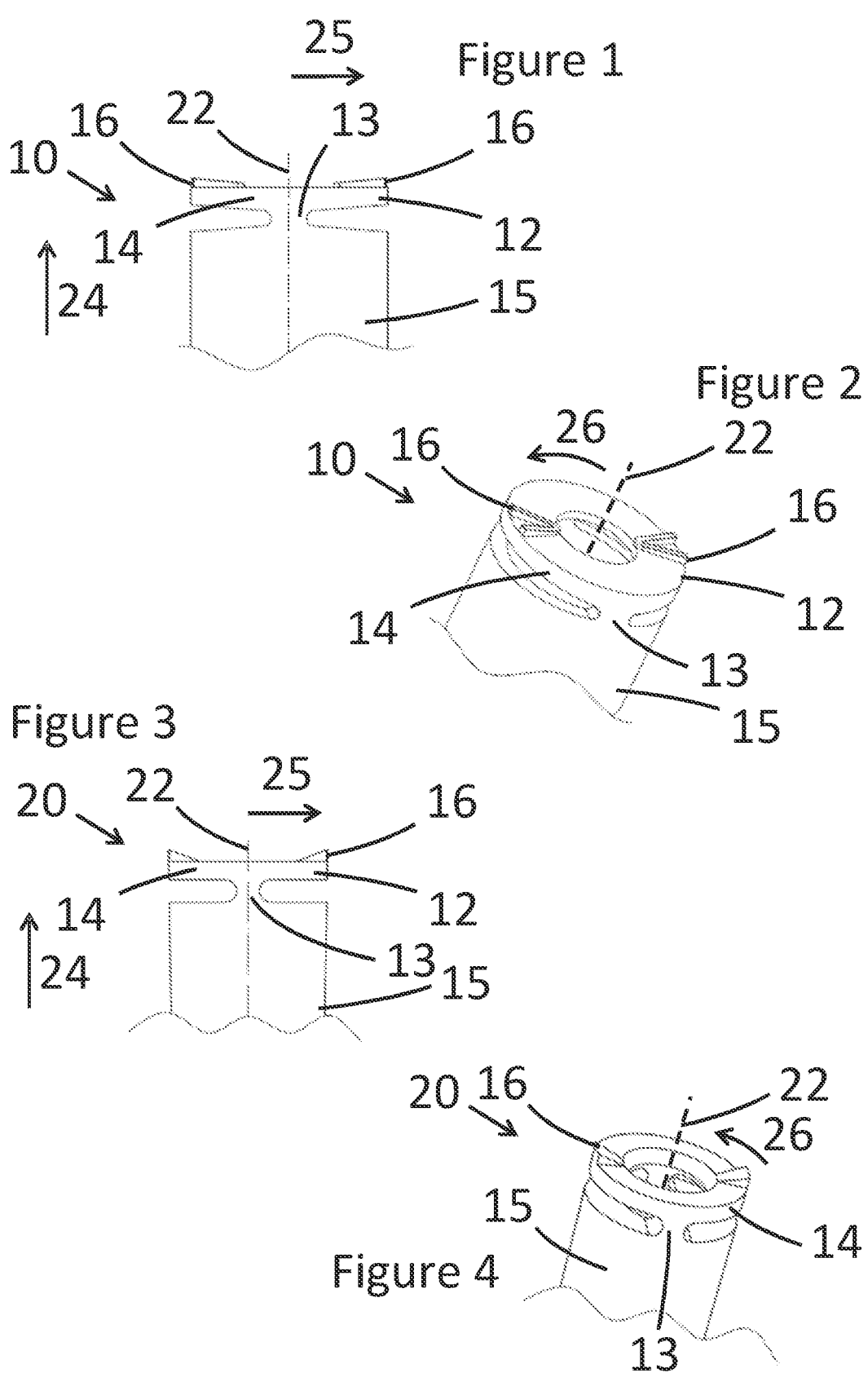
FIG. 1 shows a side view of a first example of a medicament delivery device component.
FIG. 2 shows a perspective view of the first example of a medicament delivery device component.
FIG. 3 shows a side view of a second example of a medicament delivery device component.
FIG. 4 shows a perspective view of the second example of a medicament delivery device component.

A first example of a medicament delivery device component 10 is shown in FIGS. 1 and 2. The medicament delivery device component extends in an axial direction 24 along an axis 22, and extends around the axis in a circumferential direction 26. The medicament delivery device component comprises a base portion 15 and a compensation member 12.

The compensation member can be considered as two separate portions, namely a first portion 13 attached to the base portion 15 and a second portion 14 attached to the first portion 13. The second portion 14 is spaced apart from the base portion 15 in the axial direction 24. The second portion 14 is configured to flex relative to the base portion 15 when acted on by a force in the axial direction 24.

In the example in FIGS. 1 and 2, the second portion 14 is disc-shaped, with the disc of the second portion extending around the axis in the circumferential direction in a plane perpendicular to the axis 22 when in an unbiased state, although the disc is not necessarily in a plane perpendicular to the axis 22 in some embodiments. The disc is attached to two first portions 13, which are opposite each other relative to the axis 22. Two protrusions 16 are provided. The protrusions 16 extend from the disc in the axial direction and are spaced apart from the first portion of the compensation member in the circumferential direction. The protrusions 16 are spaced apart from the base portion 15 (at least when unbiased) and extend from the disc in the axial direction. Although various shapes of protrusion could be provided, the example portrayed in FIGS. 1 and 2 has protrusions that are V-shaped, with the V extending in a radial direction 25 relative to the axis, and with the point where the two halves of the V meet being the part of the V closest to the axis. In this particular example, the portion of the protrusion furthest from the axis extends further in the axial direction than the portion of the protrusion closest to the axis, although this is optional.

A second example of a medicament delivery device component 20 is shown in FIGS. 3 to 5. The structure is generally similar to the embodiment in FIGS. 1 and 2. One difference is that the medicament delivery device component 20 has a wedge-shaped protrusion rather than the V-shaped protrusion of FIGS. 1 and 2. The wedge is sloped so that the portion of the protrusion furthest from the axis extends furthest in the axial direction, and the portion of the protrusion closest to the axis extends the least in the axial direction.

A third example of a medicament delivery device component 30 is shown in FIGS. 6 to 8. In this example, the compensation member is the same as the compensation member in FIG. 1, and the base portion is a second compensation member 35. As with the compensation member, the second compensation member 35 has a first portion 33 and a second portion 34. The first portion 33 of the second compensation member 35 is attached to the first portion 13 of the compensation member 12. The second portion 34 of the second compensation member 35 is attached to the first portion 33 of the second compensation member 35 and is spaced apart from the compensation member 12 in the axial direction 24 (at least when unbiased). The second portion 34 of the second compensation member 35 is configured to flex relative to the compensation member 12 when acted on by a force in the axial direction 24. In the example in FIGS. 6 to 8, two protrusions 36 extend in the axial direction 24 from the second compensation member 35.

Figures 9, 10, 11, 12:
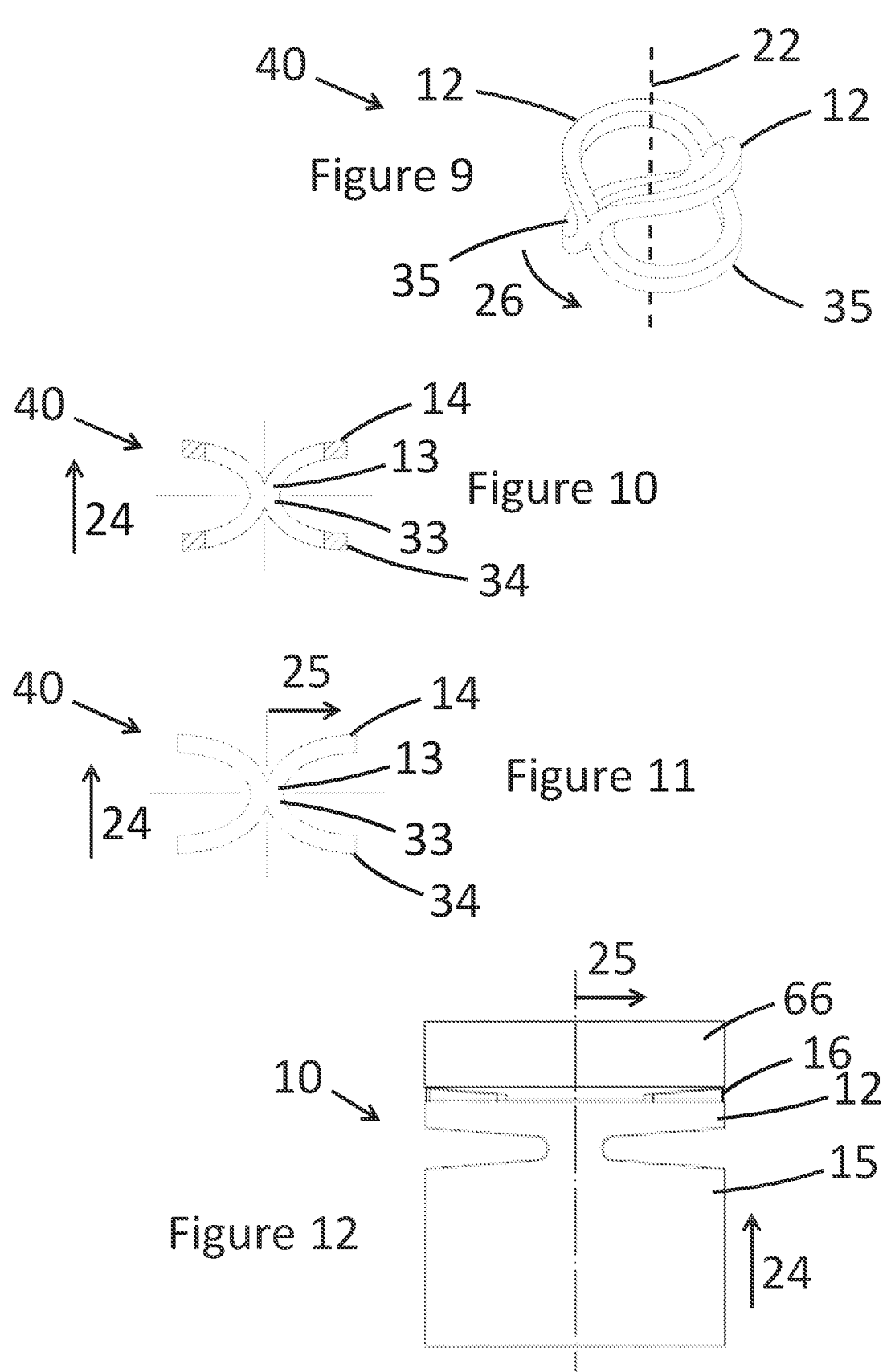
FIG. 9 shows a perspective view of a fourth example of a medicament delivery device component.
FIG. 10 shows a cross-sectional side view of the fourth example of a medicament delivery device component.
FIG. 11 shows a side view of the fourth example of a medicament delivery device component.
FIG. 12 shows a side view of the first example of a medicament delivery device component with another component.

A fourth example of a medicament delivery device component 40 is shown in FIGS. 9 to 11. As with the example in FIGS. 6 to 8, a compensation member 12 and a second compensation member 35 are provided. In this example, the compensation member is a different shape from the previous examples, with the compensation member comprising two arcs instead of a disc. The second compensation member is the same shape as the compensation member. In this particular example, the arcs extend in the axial and circumferential directions, with the arcs extending primarily in the axial direction proximal to the point in the axial direction where the compensation member and the second compensation member are attached together, and then curving to extend primarily in the circumferential direction at a point distal to the point in the axial direction where the compensation member and the second compensation member are attached together.

Figure 13:
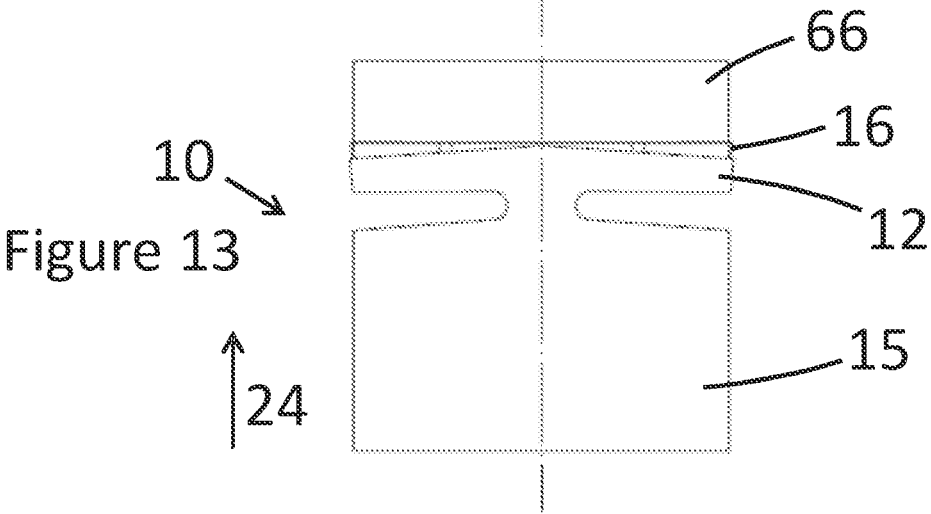
FIG. 13 shows a side view of the first example of a medicament delivery device component with another component.
Figure 14:
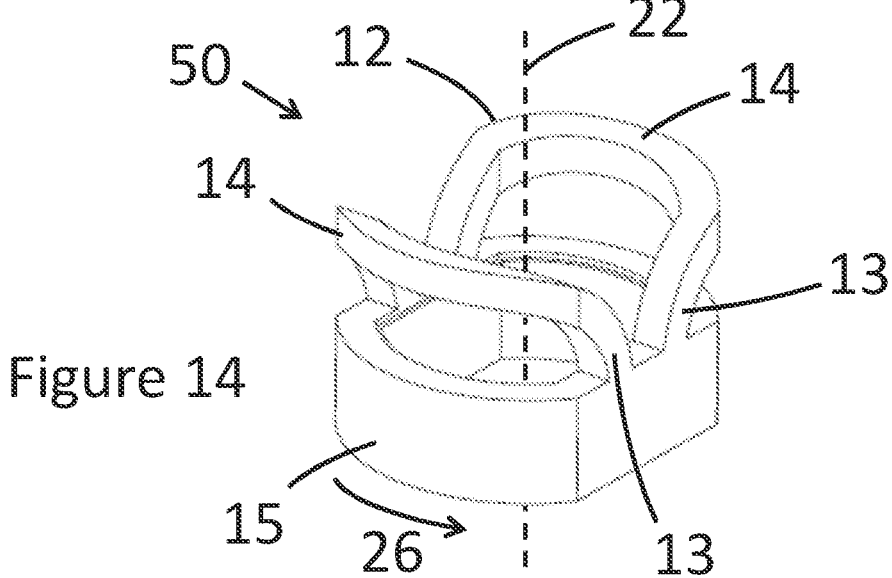
FIG. 14 shows a perspective view of a fifth example of a medicament delivery device component.

The typical working of medicament delivery device components as described herein will now be described, with reference in particular to the first example (FIGS. 1 to 2), along with FIGS. 12 and 13, which show the medicament delivery device component 10 with another component 66 abutting the medicament delivery device component 10. Component 66 could be any one of various other medicament delivery device components, for example a housing, a medicament container or a medicament container holder. In FIG. 12, the component 66 is touching the protrusions 16, but there is little or no force pushing the component 66 against the medicament delivery device component 10, and the second portion 14 of the compensation member 12 is therefore in an unbiased state—it is not flexed (examples of biased states can be seen in FIG. 13 for example, and in FIG. 17, where an unbiased state is shown in solid lines and a biased state is shown in dotted lines). Once the component 66 is pushing harder against the protrusions 16 (which would typically first happen during device assembly, for example), the compensation member flexes as shown in FIG. 13, with the amount of flex dependent in particular on the force applied and on the properties of the compensation member. The intention is typically that the compensation member is flexed to some extent in an assembled medicament delivery device, so as to avoid rattling of the components. As the compensation member can flex to different extents, the medicament delivery device component can extend a different length in the axial direction depending on the level of flex, allowing for compensation of manufacturing tolerance whilst still avoiding rattling. The compensation member would typically continue to exert a force on the component 66 after assembly, which can maintain a tight fit between components and continue to avoid rattling during transport and use. The compensation member would typically flex so that at least part of the compensation member (typically including at least part of the second portion of the compensation member, including the protrusions in embodiments with protrusions) is closer to the base portion when in a biased position than when in an unbiased position.

In the example in FIGS. 12 and 13, the protrusions 16 are initially only touching the component 66 at one point, namely the part of the protrusion furthest from the axis 22 in the radial direction 25 (see FIG. 12). In other words, the surface of the protrusion that faces the adjacent component 66 is angled relative to the shape of the adjacent component when the compensation member is unbiased (i.e. not flexed relative to the base of the medicament delivery device component). When the compensation member 12 has flexed to the position shown in FIG. 13 due to the force exerted by the component 66, a greater surface of the protrusions 16 is in contact with the component 66 due to the sloped shape of the surface of the protrusion facing the component 66. This can reduce the stress on the protrusions 16 and on the component 66.

Figure 15:
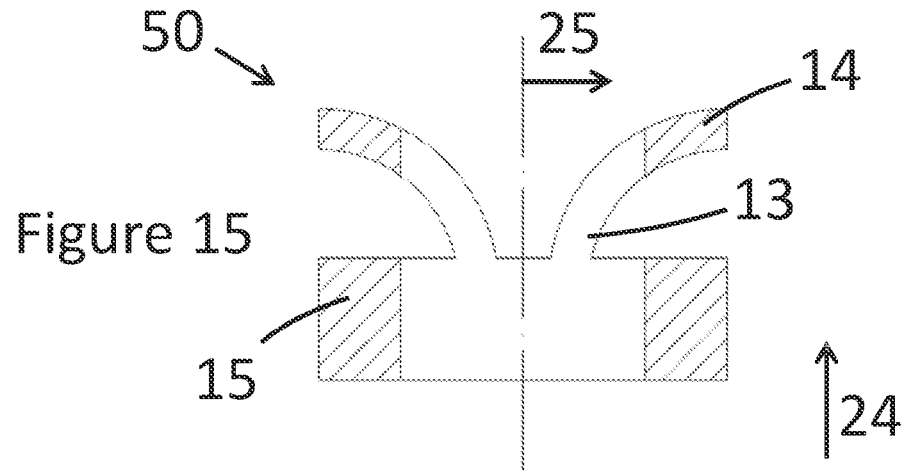
FIG. 15 shows a cross-sectional side view of the fifth example of a medicament delivery device component.
Figure 16:
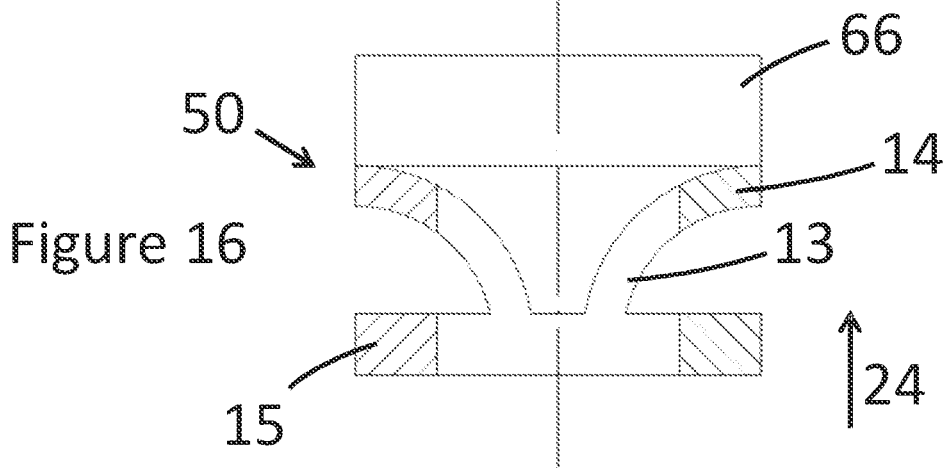
FIG. 16 shows a cross-sectional side view of the fifth example of a medicament delivery device component with another component.
Figure 17:
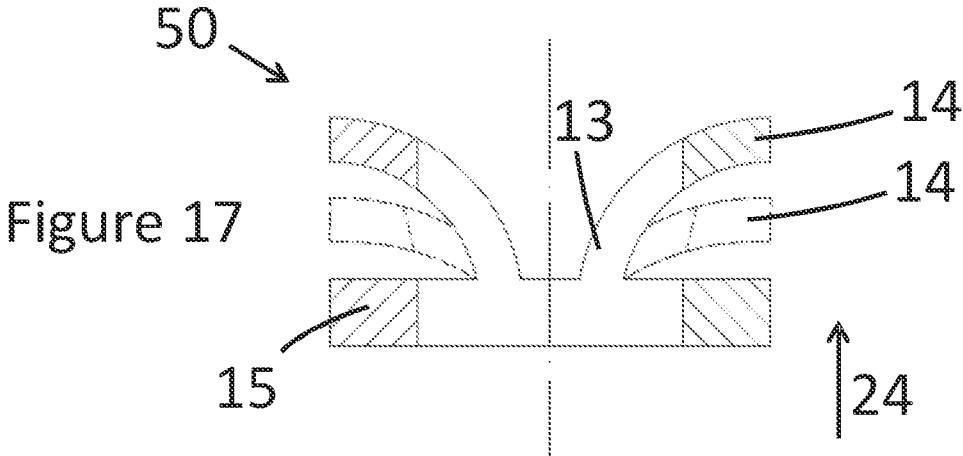
FIG. 17 shows a cross-sectional side view of the fifth example of a medicament delivery device component before and after flexing.

In a fifth example, FIGS. 14 to 17 show another medicament delivery device component 50 (although FIGS. 16 and 17 show a slightly different example from FIG. 15, since the width of the base portion 15 in the axial direction 24 varies). In this case, the compensation member 12 comprises two separate arcs, and the base portion 15 is a ring or a disc extending around the axis 22. Each arc comprises first and second portions 13, 14. As with the arcs of the fourth example, the arcs of the fifth example extend in the axial and circumferential directions, with the arcs initially extending primarily in the axial direction proximal to the point in the axial direction where the compensation member and the base portion 15 are attached together, and then curving to extend primarily in the circumferential direction at a point distal to the point in the axial direction where the compensation member and the second compensation member are attached together.

Figures 18, 19, 20:
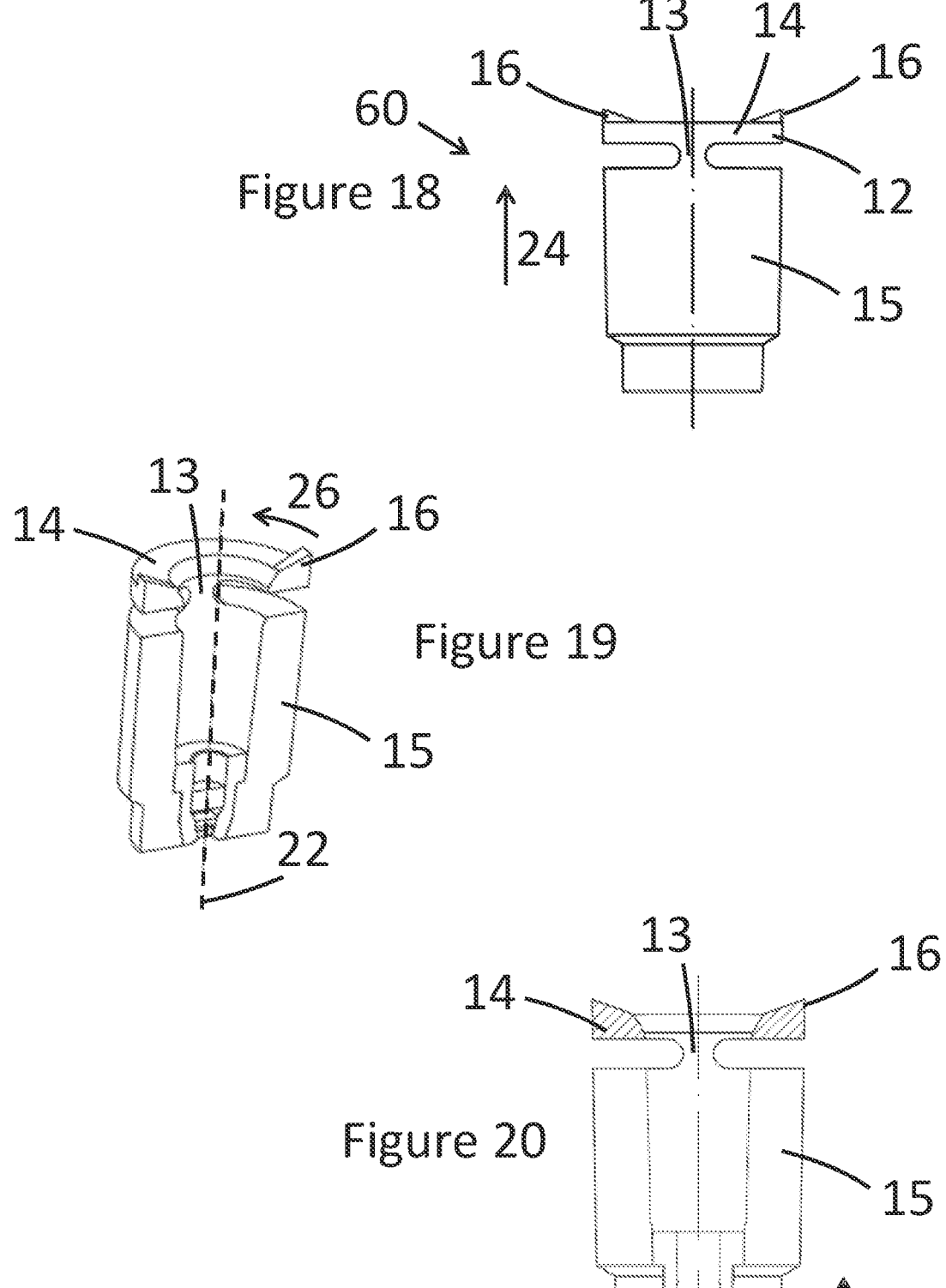
FIG. 18 shows a side view of a sixth example of a medicament delivery device component.
FIG. 19 shows a cross-sectional perspective view of the sixth example of a medicament delivery device component.
FIG. 20 shows a cross-sectional side view of the sixth example of a medicament delivery device component.

In a sixth example, FIGS. 18 to 20 show another medicament delivery device component 60. The main features of the sixth example are equivalent to the second example, but with a differently shaped base portion. In this example, the base portion is nozzle shaped so that it can accommodate a sieve and the proximal end of a medicament container.

Figures 23, 24:
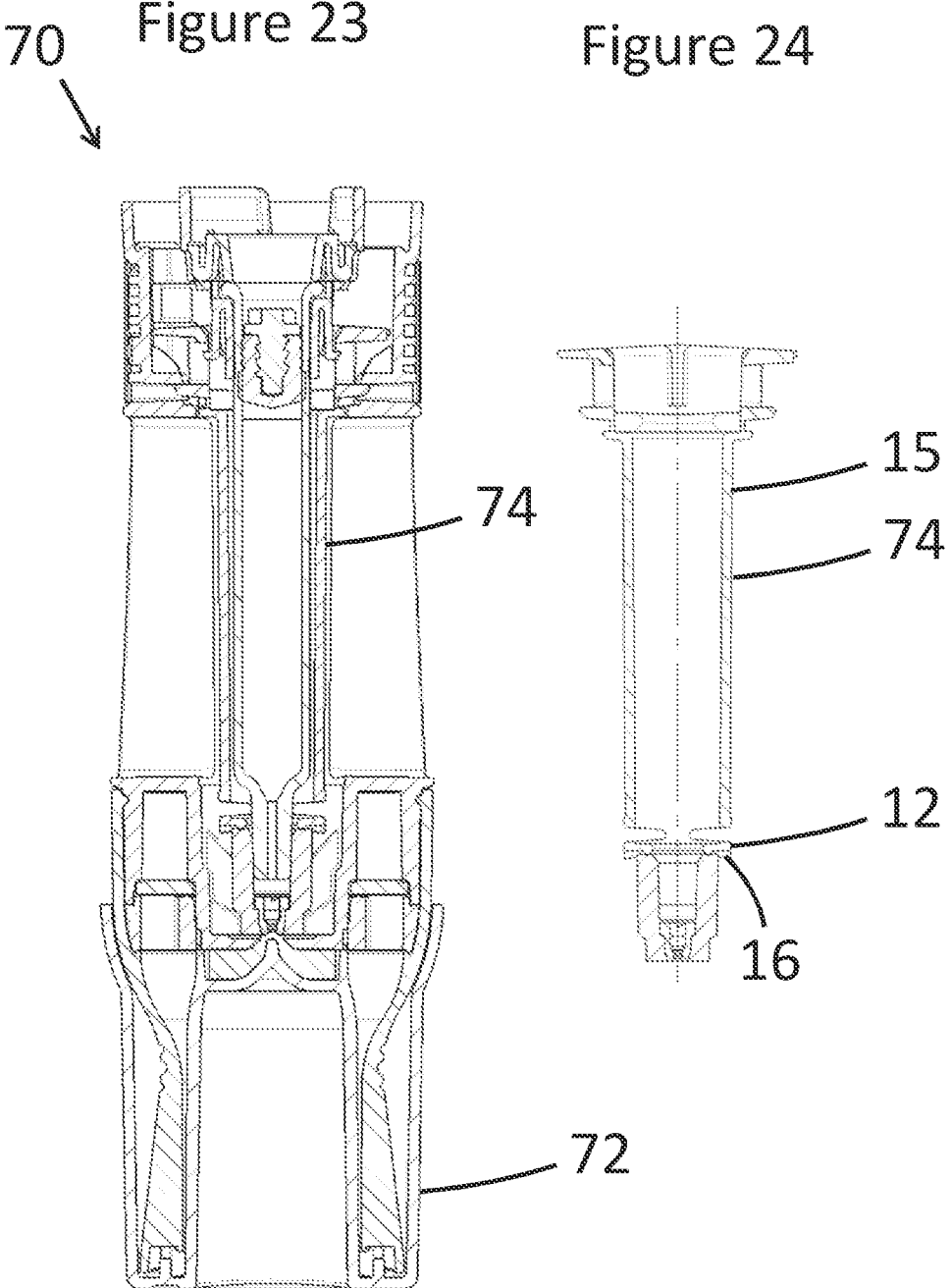
FIG. 23 shows a cross-sectional side view of part of the inhaler of FIG. 21.
FIG. 24 shows a cross-sectional side view of part of the inhaler of FIG. 21.

FIGS. 21 to 24 show an example of an inhaler in which medicament delivery device components such as those described herein could be used. The full details of the functioning of the device are not directly relevant to describing the present disclosure at hand, so will not be described herein. In FIG. 21, a complete aqueous droplet inhaler 70 is shown. FIGS. 22 and 23 show portions of the inhaler 70 in more detail, with a cap 72 shown apart from the rest of the device in FIG. 22 and the cap 72 shown on the device in FIG. 23. FIG. 24 primarily shows a medicament container holder 74, which is an example of a medicament delivery device component. The base portion 15, the compensation member 12 and a protrusion 16 are labelled in FIG. 24. In general, one or more medicament delivery device components as described herein can be included in an inhaler such as this to provide compensation for manufacturing tolerances.

Figures 25, 26:
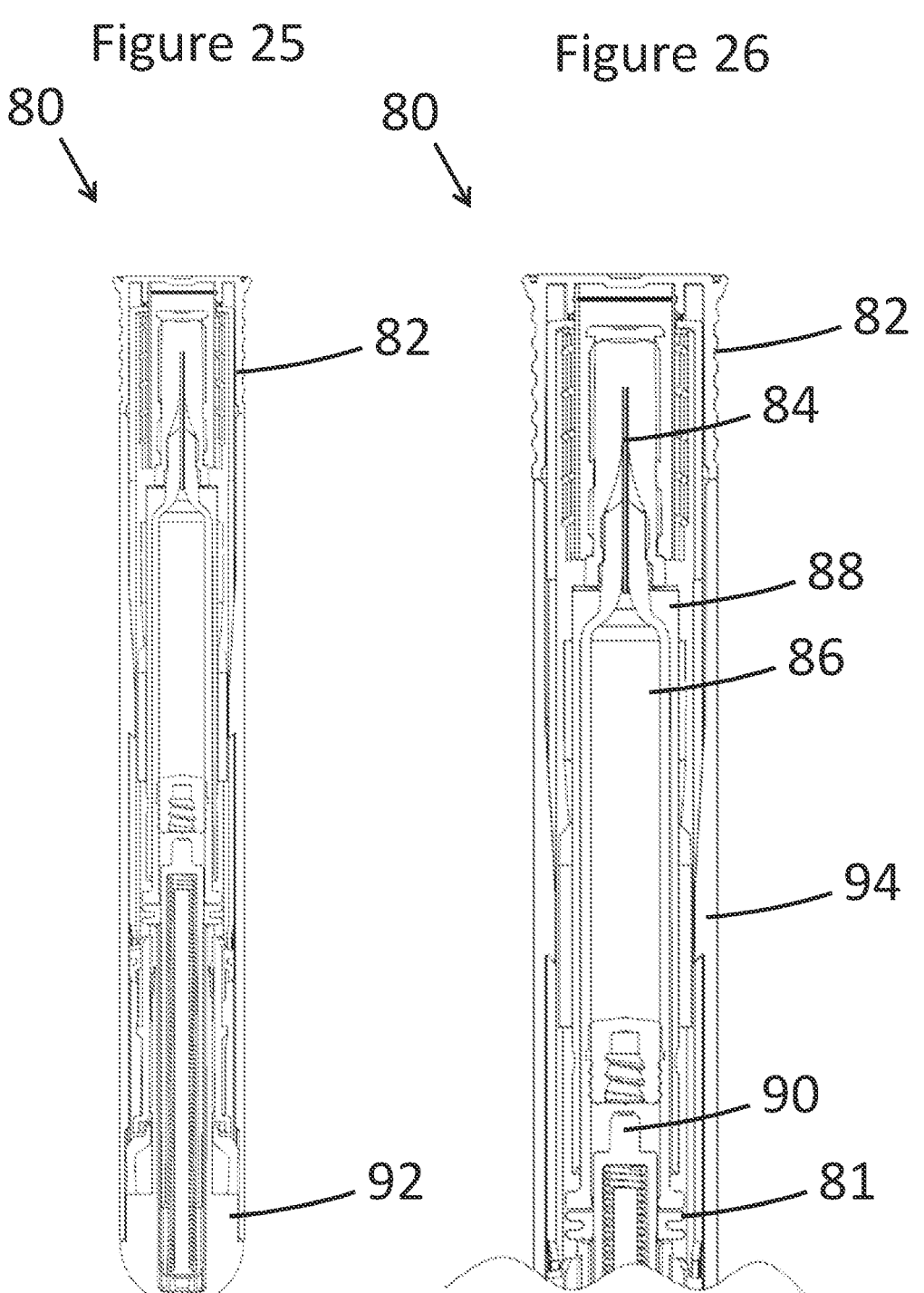
FIG. 25 shows a cross-sectional side view of an injector in which a medicament delivery device component as described herein could be used.
FIG. 26 shows a cross-sectional side view of part of the injector of FIG. 25.

FIGS. 25 and 26 show an example of an injector, in this case an auto-injector 80. Amongst other things, the auto-injector 80 comprises a medicament delivery device component 81, a cap 82, a medicament delivery member (in this case a needle 84), a medicament container 86, a medicament container holder 88, a plunger 90 (where the plunger is part of a powerpack 92), and a housing 94. One or more medicament delivery device components as described herein can be included in an injector such as this to provide compensation for manufacturing tolerances, in this case in between the powerpack 92 and the medicament container 86.

The medicament delivery device components described herein can be used in various medicament delivery devices. Example medicament delivery devices include injectors such as pen injectors or auto-injectors and inhalers. Within a medicament delivery device, two main classes of component are envisioned, namely standalone components such as those in FIGS. 6, 9 and 14, where the component is generally only provided for compensation, and combination or multi-function components such as those in FIGS. 1, 18 and 24, where the component also has a second function, such as providing the medicament container holder as shown in FIG. 24 (primarily with the base portion of the component, although the compensation portion could additionally or alternatively have other purposes beyond providing compensation). Standalone components typically consist of a compensation member and a second compensation member (or a simple base and a compensation member as in FIGS. 14 to 17).

Typically, the medicament delivery device components described herein would be integrally formed as a single part, for example by injection moulding or 3D printing, but could also be made as two or more separate pieces and attached together.

The medicament delivery device component is shown spaced apart from the central axis in all the figures, resulting in a central core space. In other words, the medicament delivery device component is tubular in many embodiments (see e.g. FIGS. 2 and 19). This typically means that the structure of the medicament delivery device component is spaced apart from the axis. Whilst this design would be typical in cases where a component such as a plunger (see FIG. 26 for example) extends inside a number of other components in the medicament delivery device, the provision of a central core space is not essential, and in some embodiments, some or all of the parts of the medicament delivery device component (for example the base portion and/or the second part of the compensation member) may extend to the axis, and may also extend in such a way that there is no hole through the centre of the component.

Some of the examples described herein provide a compensation member and second compensation member, which are typically shown as being the same (e.g. FIG. 6), but they can also differ from one another. For example, the protrusions on the compensation member could differ from the protrusions on the second compensation member so as to conform to the shape of the adjacent components at either side of the medicament delivery device component.

The compensation member is generally adjacent to the base portion in the axial direction. In the examples herein, the compensation member of each medicament delivery device component has two first portions, and the first portions are spaced apart in the circumferential direction from one another and are opposite each other relative to the axis. In other embodiments, one, three or more first portions could be provided. When two or more first portions are provided, the first portions may be the same or different from one another, and the first portions may be spaced regularly or irregularly relative to one another in the circumferential direction, and can be (but do not need to be) opposite one another relative to the axis.

The second portion 14 would typically extend all the way around the axis 22 in the circumferential direction 26, as shown in many of the figures described herein. However, the second portion can also extend only part of the way around the axis (see for example FIG. 14). As is already evident from the varied shape of the second portion in the various embodiments, the shape of the second portion can vary considerably as well.

The base portion 15 can primarily be a supporting portion for the compensation member (e.g. FIG. 14), or can provide further functionality within the same component (e.g. FIG. 18). The base portion can also be a second compensation member (e.g. FIG. 9).

In the examples, two protrusions 16, 36 are provided on a compensation member. Alternatively, the examples could be amended to provide a different number of protrusions. In general, one, three or more protrusions may be provided on a compensation member instead of two. The protrusions may be regularly or irregularly spaced around the axis in the circumferential direction. The protrusions are shown extending in the axial direction from a face of the second portion that faces away from the base portion in various embodiments (FIG. 2 and FIG. 18, for example), but could alternatively or additionally be on a face of the second portion that faces towards the base portion in some embodiments. For example, a disc-shaped second compensation member such as the one in FIG. 2 (which is a planar disc) could be bent so that the disc is not planar and the part of the disc spaced apart from the first portion in the circumferential direction is further from the base than the part of the disc at the same place as the first portion in the circumferential direction. When a force is applied to the second portion in the axial direction, the disc would flatten towards being planar. Protrusions facing the base portion could then provide support for the disc, allowing for a better distribution of load)

Various modifications to the embodiments described are possible and will occur to those skilled in the art without departing from the present disclosure which is defined by the following claims.

The invention claimed is:

1. A medicament delivery device component that compensates for manufacturing tolerances, the medicament delivery device component comprising:

a base portion extending in an axial direction along the longitudinal axis of the medicament delivery device component; and a compensation member comprising, a first portion attached to the base portion; and a second portion attached to the first portion and spaced apart from the base portion in the axial direction, wherein the second portion comprises a disc extending around the longitudinal axis in a circumferential direction and a protrusion extending from the disc in the axial direction, where the protrusion is spaced apart from the first portion in the circumferential direction, and wherein the protrusion is V-shaped having a first straight portion and a second straight portion that converge at a vertex of the V-shaped protrusion, and wherein the first straight portion and the second straight portion diverge from one another radially away from the longitudinal axis, such that the vertex is radially closer to the longitudinal axis than the remainder of the V-shaped protrusion; and wherein at least part of the disc is configured to flex relative to the base portion when acted on by a force in the axial direction.

2. The medicament delivery device component of claim 1, wherein the disc extends around the longitudinal axis in a plane perpendicular to the longitudinal axis when the disc is in an unbiased state.

3. The medicament delivery device component of claim 1, wherein the base portion is tubular.

4. The medicament delivery device component of claim 1, wherein the protrusion extends from a face of the disc, wherein the face of the disc faces away from the base portion.

5. The medicament delivery device component of claim 1, wherein the portion of the protrusion furthest from the longitudinal axis extends further from the base portion than the portion of the protrusion closest to the longitudinal axis, wherein the distance between the portion of the protrusion furthest from the longitudinal axis decreases at a constant rate.

6. The medicament delivery device component of claim 1, wherein the base portion is a second compensation member, wherein the second compensation member is on a different axial plane than the compensation member, the second compensation member comprising:

a first portion of the second compensation member, wherein the first portion of the second compensation member is attached to the first portion of the compensation member, and a second portion of the second compensation member, wherein the second portion of the second compensation member is attached to the first portion of the second compensation member and is spaced apart from the compensation member in the axial direction.

7. The medicament delivery device component of claim 6, wherein the second portion of the second compensation member comprises a disc extending around the longitudinal axis in the circumferential direction and a protrusion extending from the disc in the axial direction, and wherein the protrusion is spaced apart from the first portion of the second compensation member in the circumferential direction.

8. A medicament delivery device component for compensating for manufacturing tolerance, the medicament delivery device component comprising:

a compensation member and a second compensation member attached to the compensation member, the medicament delivery device component extending in an axial direction along the longitudinal axis of the medicament delivery device component, the compensation member comprising a first portion and a second portion, the second compensation member comprising a first portion and a second portion, wherein the first portion of the compensation member and the first portion of the second compensation member are attached to each other, wherein the second portion of the compensation member is attached to the first portion of the compensation member and is spaced apart from the second compensation member in the axial direction when the medicament delivery device component is in an unbiased state, and wherein the second portion of the compensation member is configured to flex relative to the second compensation member when acted on by a force in the axial direction, wherein the second portion of the second compensation member is attached to the first portion of the second compensation member and is spaced apart from the compensation member in the axial direction when the medicament delivery device component is in an unbiased state, and wherein the second portion of the second compensation member is configured to flex relative to the compensation member when acted on by a force in the axial direction, and wherein the medicament delivery device component comprises a protrusion extending from the second portion of the compensation member and a protrusion extending from the second portion of the second compensation member, and wherein each of the protrusion extending from the second portion of the compensation member and the protrusion extending from the second portion of the second compensation member is V-shaped and having a first straight portion and a second straight portion that converge at a vertex of the V-shaped protrusion, and wherein the first straight portion and the second straight portion diverge from one another radially away from the longitudinal axis, such that the vertex is radially closer to the longitudinal axis than the remainder of the V-shaped protrusion.

9. The medicament delivery device component of claim 8, wherein the protrusion extending from the second portion of the compensation member extends in the axial direction, and wherein the protrusion is spaced apart from the first portion of the second compensation member in the circumferential direction.

10. The medicament delivery device component of claim 8, wherein the protrusion extending from the second portion of the second compensation member extends in the axial direction, and wherein the protrusion is spaced apart from the first portion of the compensation member in the circumferential direction.

11. The medicament delivery device component of claim 6, wherein the medicament delivery device component consists of the compensation member and the second compensation member.

12. The medicament delivery device component of claim 6, wherein the compensation member is the same shape as the second compensation member.

13. The medicament delivery device component of claim 1, wherein the medicament delivery device component is a single integrally formed part.

14. A medicament delivery device comprising the medicament delivery device component of claim 13.

15. The medicament delivery device of claim 14, wherein the medicament delivery device is an inhaler, an auto-injector or a pen injector.

16. A medicament delivery device component that compensates for manufacturing tolerances, the medicament delivery device component comprising: a base portion extending in an axial direction along the longitudinal axis of the medicament delivery device component, where the base portion is tubular;

a compensation member comprising, a first portion attached to the base portion and a second portion attached to the first portion and spaced apart from the base portion in the axial direction, wherein the second portion comprises a disc extending around the longitudinal axis in a circumferential direction in a plane perpendicular to the longitudinal axis in a first unbiased state, wherein the disc comprises two protrusion that extend from a surface in the axial direction, where the protrusions are spaced apart from the first portion and from each other in the circumferential direction, and wherein each of the protrusions is V-shaped having a first straight portion and a second straight portion that converge at a vertex of the V-shaped protrusion, and wherein the first straight portion and the second straight portion diverge from one another radially away from the longitudinal axis, such that the vertex is radially closer to the longitudinal axis than the remainder of the V-shaped protrusion; and wherein the disc moves from the unbiased state to a flexed state relative to the base portion when acted on by a force in the axial direction.

17. The medicament delivery device component of claim 16, wherein the portion of each of the protrusions furthest from the longitudinal axis extends further from the base portion than the portions of the protrusions closest to the longitudinal axis, wherein the distance between the portion of the protrusion furthest from the longitudinal axis decreases at a constant rate.

18. The medicament delivery device component of claim 16, wherein the base portion comprises a second compensation member, wherein the second compensation member is on a different axial plane than the compensation member, the second compensation member comprising:

a first portion of the second compensation member, wherein the first portion of the second compensation member is directly attached to the first portion of the compensation member; and a second portion of the second compensation member, wherein the second portion of the second compensation member is attached to the first portion of the second compensation member and is spaced apart from the compensation member in the axial direction.

* * * * *